United States Patent [19]

Johnson et al.

[11] Patent Number: 5,664,455

[45] Date of Patent: Sep. 9, 1997

[54] LABORATORY DEVICE TO ASSIST IN THE SIMULATION OF SYNTHETIC FIBER HEAT-SETTING CONDITIONS

[75] Inventors: Ann S. Johnson, Asheville; John A. Kilpatrick; Lewis W. Davis, Jr., both of Candler; David B. Ledford, Arden; Larry D. Henderson, Waynesville; Phillip E. Wilson, Asheville, all of N.C.

[73] Assignee: BASF Corporation, Mount Olive, N.J.

[21] Appl. No.: 476,585

[22] Filed: Jun. 7, 1995

[51] Int. Cl.$^6$ ........................................... G01N 3/60
[52] U.S. Cl. ........................ 73/160; 73/159; 374/57; 19/65 A
[58] Field of Search ............... 73/159, 160, 865.6, 73/866; 374/45, 57; 19/65 A; 26/106; 38/102.1, 102.9, 70; 5/186.1, 190, 191, 187, 199, 200.1

[56] References Cited

U.S. PATENT DOCUMENTS

| | | | |
|---|---|---|---|
| 278,330 | 5/1883 | Graves | 5/199 |
| 339,789 | 4/1886 | Kilburn | 5/200.1 |
| 2,355,635 | 8/1944 | Oubiliar | 5/186.1 |
| 2,490,134 | 12/1949 | Jennings | 73/160 |
| 3,840,913 | 10/1974 | Feische | 5/186.1 |
| 4,407,164 | 10/1983 | Imlah | 73/159 |
| 4,572,243 | 2/1986 | Felix | 73/160 |
| 4,956,885 | 9/1990 | Alich et al. | 5/431 |

*Primary Examiner*—William A. Cuchlinski, Jr.
*Assistant Examiner*—Andrew Hirshfeld
*Attorney, Agent, or Firm*—Nixon & Vanderhye P.C.

[57] ABSTRACT

A laboratory-scale device for assisting in the simulation of heat setting conditions includes a pair of laterally spaced-apart flexible heat-resistant cords (e.g., formed of aramid fibers) tensioned between forward and rearward rigid cross-support bars. At least one rigid tensioning bar is provided parallel to the support cords and extending between the cross-support bars so as to maintain the desired tension on the flexible heat-resistant cords. The tensioning bar thus allows for manual or automated lateral winding of the synthetic heat-settable fibers or yarns about the spaced-apart heat-resistant cords during preparation of the device for a laboratory test run. The tensioning bar may thereafter be removed once the device has been secured in position with the laboratory heat-setting oven. In such a manner, therefore, various effects on heat-setting conditions simulating can be investigated.

17 Claims, 2 Drawing Sheets

5,664,455

LABORATORY DEVICE TO ASSIST IN THE SIMULATION OF SYNTHETIC FIBER HEAT-SETTING CONDITIONS

FIELD OF INVENTION

The present invention relates generally to laboratory devices. In preferred forms, the present invention relates to laboratory devices which may be employed to assist in the simulation of commercial scale synthetic yarn heat-setting conditions.

BACKGROUND AND SUMMARY OF THE INVENTION

Synthetic fibers, yarns and fabrics are often subjected to heat-setting processes during manufacture so as to confer dimensional stability and other desirable properties to the finished synthetic fiber product. One well known technique is the Suessen heat-setting process which involves wrapping synthetic fibers or yarns around a moveable support frame comprised of elongate heat-resistant support cords (e.g., formed of polyaramid fibers, such as Nomex-brand fibers). The support cords forming the moveable frame thus support the synthetic fibers or yarns in a relative "open" condition where substantially no contact occurs between adjacent turns of the fibers or yarns wrapped about the support cords. Controlled conveyance through a heat-setting oven therefore imparts the desired heat-set properties to the fibers or yarns.

One problem associated with the Suessen heat-setting process is that, since the fibers are wrapped around heat-resistant support cords, some differential heat-setting conditions will be realized particularly where the fibers being heat-set come into physical contact with the support cord. Variations in yarn tension may also be present. This differential heat-setting thereby results in differential dying, coloration or crimp development of the fibers thereby causing visually perceptible color differences (known in art parlance as "chevrons") to be discernable in the finished fabric product. Using commercial scale Suessen heat-setting equipment to investigate heat-setting conditions for various synthetic fibers that may give rise to imperfections (chevrons) in the finished fabric product so that such conditions may be avoided is clearly not economically viable.

Therefore, what has been needed is a laboratory scale device which, when employed in conjunction with a laboratory scale heat-setting oven, may assist investigators in simulating heat-setting conditions so that imperfections (chevrons) in the finished fiber product may be minimized or eliminated entirely when operated on a commercial scale. It is towards providing such a device that the present invention is directed.

Broadly, therefore, the present invention is embodied in a laboratory scale device which may be used in cooperation with a laboratory scale heat-setting oven so as to simulate Suessen heat-setting conditions. In preferred forms, the present invention is embodied in a laboratory-scale device for assisting in the simulation of heat setting conditions which includes a pair of laterally spaced-apart flexible heat-resistant cords tensioned between forward and rearward rigid cross-support bars. At least one rigid tensioning bar is provided parallel to the support cords and extending between the cross-support bars so as to maintain the desired tension on the flexible heat-resistant cords. The tensioning bar thus allows for manual or automated lateral winding of the synthetic heat-settable fibers or yarns about the spaced-apart heat-resistant cords during preparation of the device for a test run. The tensioning bar may thereafter be removed once the device has been secured in position with the laboratory heat-setting oven. In such a manner, therefore, various effects on heat-setting conditions simulating the Suessen heat-setting process can be investigated without resorting to the use of full scale commercial heat-setting equipment and the resulting idled production from such use.

Further aspects and advantages will become more clear after careful consideration is given to the following detailed description of the preferred exemplary embodiments thereof.

BRIEF DESCRIPTION OF THE ACCOMPANYING DRAWINGS

Reference will hereinafter be made to the accompanying drawings wherein like reference numerals throughout the various FIGURES denote like structural elements, and wherein.

DETAILED DESCRIPTION OF THE PREFERRED EXEMPLARY EMBODIMENTS

Figure 1:
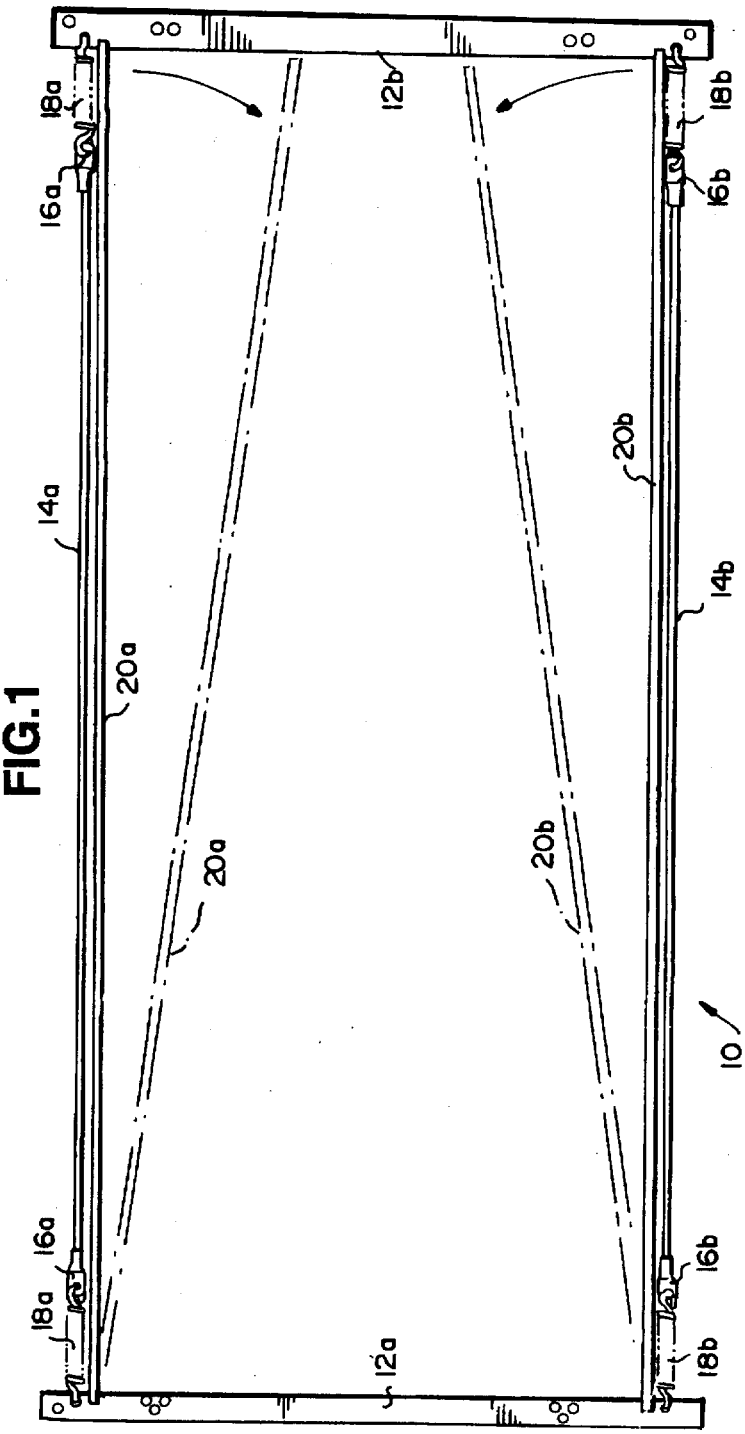
FIG. 1 is a top plan view of the device according to this invention.

Accompanying FIG. 1 depicts the laboratory device 10 according to this invention in plan view. As is seen, the device 10 is comprised of forward and rearward cross-support bars 12a, 12b between which a pair of laterally spaced-apart heat-resistant support cords 14a, 14b extend. Although the overall dimensions of the device 10 are not critical, it is presently preferred that the length of the support cords 14a, 14b is about twice the length of the cross-support bars 12a, 12b so that the device has an overall length about twice its overall width.

The ends of each support cord 14a, 14b terminate in an eyelet connector 16a, 16b which are, in turn, connected to a respective adjacent cross-support bar 12a, 12b by tension springs 18a, 18b, respectively. The tension springs 18a, 18b thus serve to maintain adequate tension on the support cords 12a, 12b when the device 10 is placed in service during a heat-setting trial.

In order to facilitate cross-winding of a synthetic fiber or yarn around and between the laterally spaced-apart support cords 14a, 14b, the device of this invention is provided with a pair of elongate rigid tensioning bars 20a, 20b which are of sufficient length so as to maintain the longitudinal separation of the cross-support members 12a, 12b and thereby maintain slight tension on the springs 18a, 18b, and thus the support cords 14a, 14b. The tensioning bars 20a, 20b are most preferably positioned interiorly adjacent and parallel to the support cords 14a, 14b, respectively, so that the synthetic fibers or yarns to be heat-set may be wound about one support cord 14a to the next support cord 14b in successive turns. The synthetic fibers or yarns to be heat set will thus be wound around the support cords 14a, 14b such that the wound synthetic fibers or yarns to be heat-set cover the space between the support cords 14a, 14b between the eyelet connectors 16a, 16b.

Figure 2:
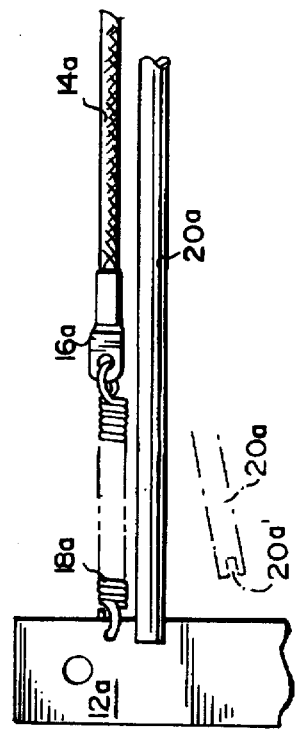
FIG. 2 is an enlarged detailed plan view showing the manner in which the support cord and the tensioning bar are coupled to the cross-support bar.

The tensioning bars 20a, 20b each are provided with notched terminal ends as shown by notch 20a' in FIG. 2 which is sized to accept therein an edge of a respective support bar 12a, 12b. Once the synthetic fibers or yarns to be heat-set have been wound around the support cords 14a, 14b, therefore, the tensioning bars 20a, 20b may be removed from the device 10 simply by moving one of the notched ends of bars 20a, 20b laterally inwardly until it is disengaged from the edge of its respective cross-support bar as shown in phantom line in FIG. 2. The tensioning bars 20a, 20b are thus set aside until needed when a fresh mount of synthetic fibers or yarns are to be heat-set.

Figure 3:
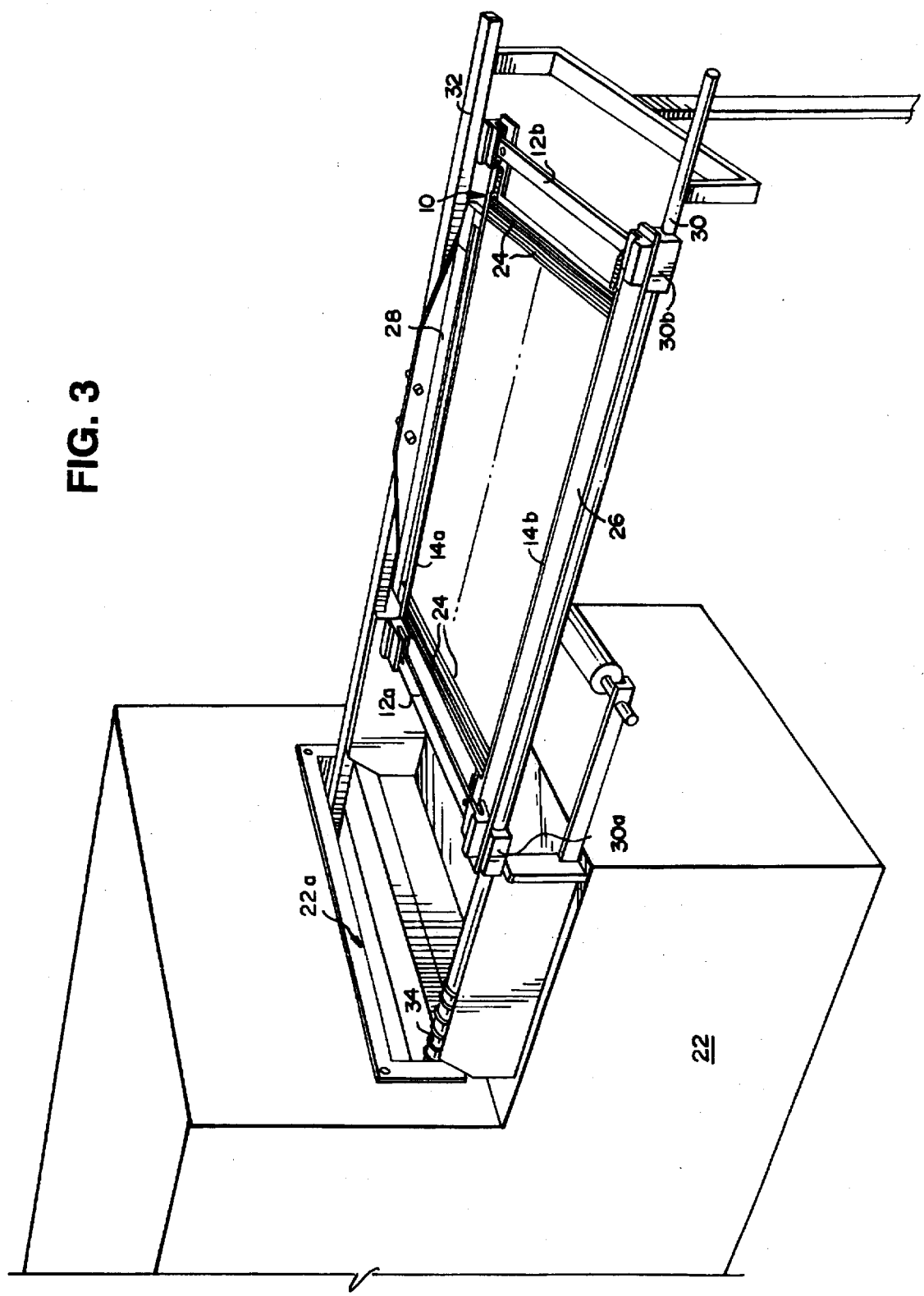
FIG. 3 is a partial perspective view showing the device according to this invention in use with a laboratory scale heat-setting oven.

The device 10 according to this invention is shown in FIG. 3 in use with a conventional laboratory scale heat-setting oven 22 (e.g., Type TKF M500 from Ernst Benz Textilmaschinen). In this regard, it will be observed in FIG. 3 that the device 10 carries a continuous length of synthetic yarn 24 wrapped around the laterally spaced-apart support cords 14a, 14b, and that the tensioning rods 20a, 20b have been removed therefrom as described above.

The ends of the cross-support bars 12a, 12b are clamped in lateral frame members 26, 28 which are slidably associated with guide rails 30, 32 extending from the inlet window 22a of the oven 22. Threaded guide blocks 30a, 30b are provided with the frame member 26 so as to be threadably coupled to the rotatable advancement screw 34. Thus, controlled rotation of the advancement screw 34 causes the frame members 26, 28, and hence the device 10, to be conveyed through the oven 22 in a controlled manner. The residence time within the oven 22 as well as the temperature conditions/profiles within the oven may be preselected to simulate on a laboratory scale heat-setting conditions that may be implemented on commercial scale equipment. In such a manner, the effects of such processing parameters on the synthetic fibers or yarns 24 can be analyzed and investigated without subjecting the commercial equipment to costly down time.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A laboratory Suessen heat-setting simulator frame for simulating effects on synthetic fibers subjected to Suessen heat-setting conditions comprising:

(i) forward and rearward rigid cross-support bars; and (ii) a laterally spaced-apart pair of flexible synthetic fiber cords which are resistant to Suessen heat-setting conditions extending in parallel to one another, said cords being connected to, and extending between, said forward and rearward cross-support bars for supporting successive wound turns of synthetic fibers to be subjected to simulated Suessen heat-setting conditions.

2. The laboratory frame of claim 1, which includes tension springs connecting each end of said flexible synthetic fiber cords to a respective one of said cross-support bars.

3. The laboratory frame of claim 2, wherein each end of said flexible synthetic fiber cords includes a connector connecting said end of said flexible synthetic fiber cords to a respective one of said tension springs.

4. The laboratory frame of claim 3, wherein each said connector is an eyelet connector.

5. The laboratory frame of any one of claims 1-4, further comprising at least one elongate tensioning rod removably connected to, and extending between, said forward and rearward cross-support bars and being of a length sufficient to maintain said flexible synthetic fiber cords under tension.

6. The laboratory frame of any one of claims 1-4, further comprising a pair of tensioning rods, wherein each end of said tensioning rods is removably connected to a respective one of said cross-support bars such that each of said tensioning rods is positioned adjacent and parallel to a respective one of said flexible synthetic fiber cords.

7. The laboratory frame of claim 6, wherein each said end of said tensioning rods includes a notch, and wherein each said notch receives an edge of a respective one of said cross-support bars to thereby removably connect said tensioning rods to said cross-support bars.

8. The laboratory frame of claim 1, wherein said cords are formed of aramid fibers.

9. The combination comprising a laboratory heat-setting oven for subjecting synthetic fibers to heat-setting conditions, and a laboratory device comprising:

(i) forward and rearward rigid cross-support bars; and (ii) laterally spaced-apart pair of heat-resistant support members extending in parallel to one another and connected between said forward and rearward cross-support bars for supporting successive wound turns of synthetic fibers to be heat-set, wherein said heat-setting oven includes a pair of laterally spaced-apart guide rails, and wherein opposed ends of said cross-support bars of said device are clamped to, and extend between, said guide rails.

10. The combination of claim 9, wherein said support members are flexible synthetic fiber cords.

11. The combination of claim 10, wherein said cords are formed of aramid fibers.

12. The combination of any one of claims 9-11, wherein said laboratory device further includes tension springs connecting each end of said support members to a respective one of said cross-support bars.

13. The combination of claim 12, wherein each said end of said support members includes a connector connecting each said end of said support members to a respective one of said tension springs.

14. The combination of claim 13, wherein each said connector is an eyelet connector.

15. The combination of any one of claims 9-11, wherein said laboratory device further includes at least one elongate tensioning rod removably connected to, and extending between, said forward and rearward cross-support bars, and being of a length sufficient to maintain said support members under tension.

16. The combination of any one of claims 9-11, wherein said laboratory device further includes a pair of elongate tensioning rods each removably connected to, and extending between, said forward and rearward cross-support bars, and being of a length sufficient to maintain said support members under tension.

17. The combination of claim 16, wherein each end of said tensioning rods includes a notch, and wherein each said notch receives an edge of a respective one of said cross-support bars.

* * * * *